United States Patent
Gorin

(10) Patent No.: US 7,258,444 B2
(45) Date of Patent: Aug. 21, 2007

(54) METHOD AND APPARATUS FOR SCREENING FOR RETINOPATHY

(75) Inventor: Michael B. Gorin, Pittsburgh, PA (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 177 days.

(21) Appl. No.: 11/232,068

(22) Filed: Sep. 21, 2005

(65) Prior Publication Data
US 2006/0077348 A1    Apr. 13, 2006

Related U.S. Application Data

(60) Provisional application No. 60/616,160, filed on Oct. 5, 2004.

(51) Int. Cl.
*A61B 3/10* (2006.01)

(52) U.S. Cl. ........................ 351/221; 351/205; 351/246

(58) Field of Classification Search ................ 351/221, 351/205, 246, 200, 209, 212, 247, 211, 210, 351/216, 219, 206
See application file for complete search history.

(56) References Cited

U.S. PATENT DOCUMENTS

| 5,490,098 A | 2/1996 | Kardon |
| 6,199,985 B1 | 3/2001 | Anderson |
| 6,582,079 B2 * | 6/2003 | Levine ..................... 351/221 |

* cited by examiner

*Primary Examiner*—Ricky Mack
*Assistant Examiner*—Tuyen Tra
(74) *Attorney, Agent, or Firm*—Philip E. Levy; Arnold B. Silverman; Eckert Seamans Cherin & Mellott, LLC

(57) ABSTRACT

A method of screening for retinal disease including directing a first light at a first portion of the retina, directing a second light at a second portion of the retina, measuring a first pupillary response of the eye as a result of the first light and a second pupillary response as a result of the second light, and generating an indication of a severity level of the retinal disease using the first pupillary response and the second pupillary response. Also, an apparatus that implements this method including a light source for directing a first light at a first retinal portion and a second light at a second retinal portion, a pupil measuring device for measuring the pupillary response of the eye as a result of the first light and second light, a processor in electronic communication with the pupil measuring device, and a memory in electronic communication with the processor.

48 Claims, 8 Drawing Sheets

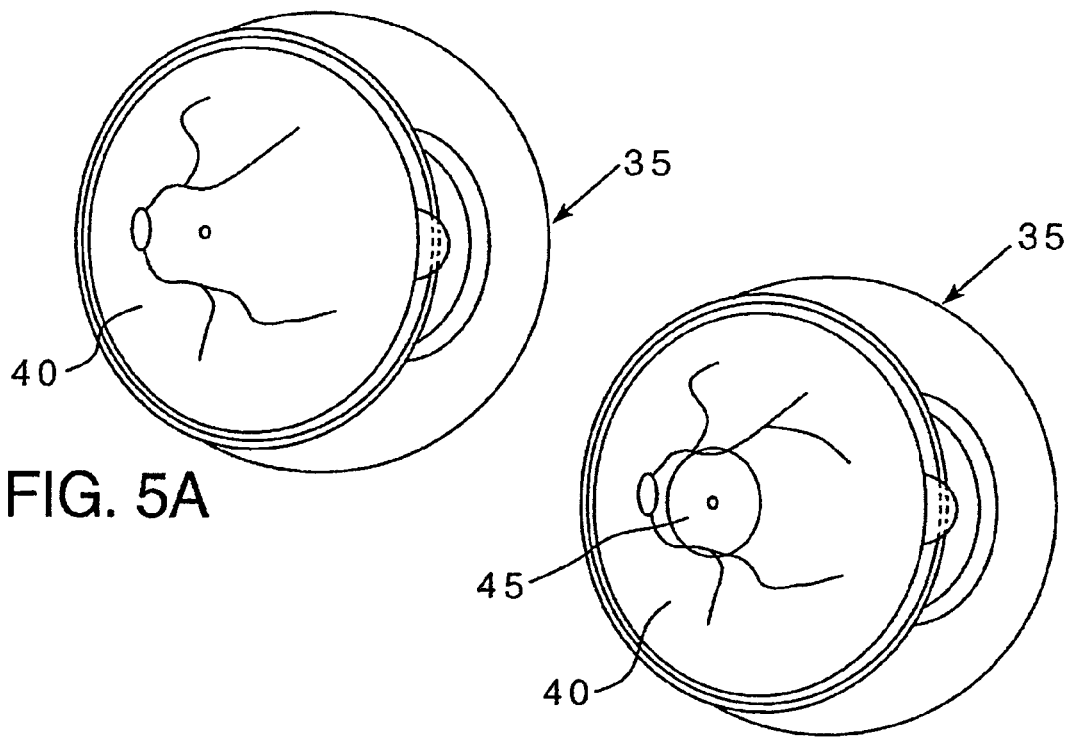
FIG. 5A
FIG. 5B
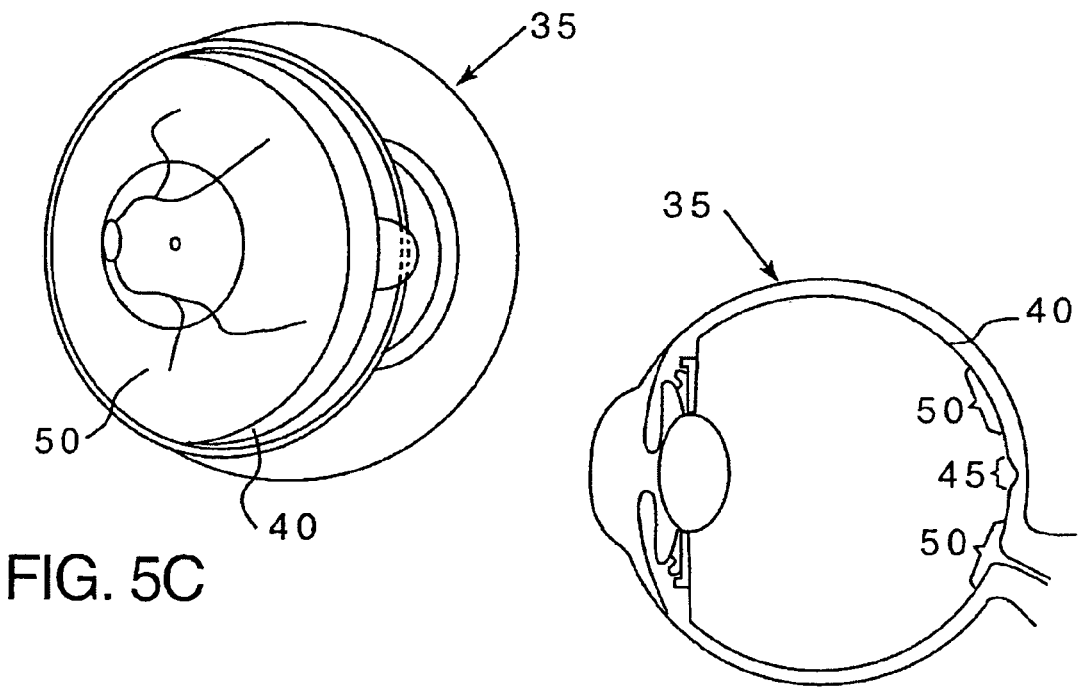
FIG. 5C
FIG. 5D

METHOD AND APPARATUS FOR SCREENING FOR RETINOPATHY

CROSS-REFERENCE TO RELATED APPLICATION

The instant application claims priority from U.S. Provisional Patent Application Ser. No. 60/616,160 filed Oct. 5, 2004, the disclosures of which are incorporated herein by reference.

BACKGROUND OF THE INVENTION

1. Field of the Invention

The present invention relates to a method and apparatus for screening for retinopathy, such as diabetic retinopathy, and in particular to a method and apparatus for providing an objective indication of the severity of retinal disease and disease features, such as diabetic retinopathy and retinal ischemia, using pupillometry and a plurality of light stimuli.

2. Description of Related Art

There is an epidemic of diabetes in this country. Diabetic retinopathy, which is a pathological disorder of the retina caused by diabetes, is a major health threat to diabetics. It is estimated that more than 80% of diabetics will develop diabetic retinopathy to some extent, with a large percentage requiring treatment. The most common cause of vision loss in diabetics is the failure to recognize and treat diabetic retinopathy. Thus, effective screening for diabetic retinopathy is essential for diabetics to maintain visual function and quality of life.

Diabetic retinopathy is the result of retinal capillary damage caused by diabetes. The progressive loss of retinal capillaries leads to areas of retinal ischemia, which is a decrease in blood supply to the retina, primarily in the midperipheral portion, and to a lesser extent in the central portion, of the retina. Retinal ischemia promotes angiogenesis, also called neovascularization, which is the growth of new blood vessels in the retina. When uncontrolled, angiogenesis can cause damage to normal retinal tissues because the new vessels are fragile and hemorrhage easily. In addition, ischemic changes promote increased permeability of the retinal blood vessels, which leads to a swelling and thickening of the central portion of the retina, a condition called macular edema (the macula is an area near the center of the retina), and reduced visual function. Midperipheral retinal ischemia, while primarily seen in diabetic retinopathy, is also seen in a number of other conditions, including sickle cell disease, retinitis pigmentosa, Eales disease, and radiation retinopathy, among others. An ischemic retina has reduced sensitivity to light in portions thereof, which is why diabetics with advanced forms of the disease are often night blind and have reduced peripheral vision.

In screening for diabetic retinopathy, a clinician thus needs to look for signs of both macular edema and midperipheral retinal ischemia. The extent of retinal thickening in the macula (macular edema) can be a quantitatively assessed using an existing technology known as optical coherence tomography (OCT). OCT provides actual dimensions of the thickness of the retina in the central 6 mm thereof, and thus can be used to detect macular edema that might adversely effect vision.

Unlike macular edema, there is currently no known quantitative screening method for retinal ischemia. Instead, current screening methods for retinal ischemia involve the subjective clinical observation of various physiological conditions including nerve fiber layer infarcts, arteriolar narrowing, venous bleeding and actual neovascularization. Studies have shown that clinical expertise has a great deal to do with the ability to recognize severe preproliferative diabetic retinopathy, and in particular retinal ischemia, through clinical examinations. This is due, in part, to the fact that the midperipheral portion of the retina is poorly visualized by routine clinical exams and most retinal photography systems. As a result, screening programs based on clinical examinations have a high no show rate, and many cases of diabetic retinopathy are not diagnosed until proliferative retinal changes are extensive.

A number of known screening systems have been devised that translate the clinical examination to an imaging effort. In such systems, images of the retina are transmitted to a reading center where they are examined by trained clinicians to assess disease features. Such systems have several disadvantages, including delays in determining patient status, since images must be transmitted to and reviewed by a remote clinician (such delays create a potential for loss of follow-up with the patient), the high manpower costs required to implement the systems, the limitations imposed by media opacities that affect the quality of the transmitted images, and the fact that such systems still rely on subjective clinical examinations and, as a result, present the same problems described above.

The most direct way to detect retinal ischemia is with a test known as a fluorescein angiogram. A fluorescein angiogram, however, is an invasive procedure that requires dilation of the eye, the injection of dye into the patient and highly specialized photography. As a result, fluorescein angiograms present the potential for numerous complications. In addition, reduced retinal light sensitivity, such as is caused by retinal ischemia, can be assessed through known techniques such as visual field testing and multifocal electrophysiology. These techniques have several disadvantages associated with them. In particular, visual field testing is subjective, time consuming, and relies on the active and accurate participation by the patient, and multi-focal electrophysiology is costly, time consuming, and requires dilation and significant patient cooperation.

Thus, there is a need for a screening approach for retinal disease and associated features, such as those that cause reduced light sensitivity in portions of the retina as is the case with retinal ischemia, that is objective, quantitative, requires minimal cooperation of the patient, requires limited technician skills, and that can provide an immediate clinical assessment.

SUMMARY OF THE INVENTION

The present invention relates to an apparatus for screening for retinal disease in an eye of a patient including a light source for directing a first light at a first portion of the retina and a second light at a second portion of the retina, a pupil measuring device for measuring a first pupillary response of the eye as a result of the first light and a second pupillary response of said eye as a result of the second light, a processor in electronic communication with the pupil measuring device, and a memory in electronic communication with the processor. The memory stores one or more routines executable by the processor that are adapted to generate an indication of a severity level of retinal disease using the first pupillary response and the second pupillary response. The key features of this instrument and method are the determination of disease severity by comparing the light responses from at least two regions of the retina and doing so in a fashion in which the method can internally control for inter-individual variability due to media clarity, intrinsic pupillary responses, and age, while detecting differences in retinal responses.

In one embodiment, the light source includes a first light source for generating the first light and a second light source for generating the second light. In addition, the first portion may be a central portion of said retina and the second portion may be a midperipheral portion of the retina, in which case the second light source may be an annulus light source with the second light being an annulus light. In a particular embodiment, the first portion of the retina is about a central ten degrees of the retina, and the second portion of the retina is an annulus of the retina that is inclusive of about twenty to fifty degrees eccentric to a fovea of the eye.

The pupil measuring device may be a pupillometer that includes an infrared light source and an infrared detector, such as an infrared camera. In addition, mirrors may be used to properly direct the infrared light.

In one particular embodiment, the one or more routines are further adapted to turn the first light source on and increase its intensity level over a plurality of first intensity levels, with the pupil measuring device making a first pupillary measurement at each of the first intensity levels, and turn the second light source on and increase its intensity level over a plurality of second intensity levels, with the pupil measuring device making a second pupillary measurement at each of the second intensity levels. In this case, the first pupillary response is based on the first pupillary measurements and the second pupillary response is based on the second pupillary measurements. Moreover, the severity level indication may be a ratio that is generated based on one of the first intensity levels and one of the second intensity levels, such as a ratio of the second intensity level to the first intensity level. The particular intensity levels used may be the second intensity level that corresponds to a particular level of the second pupillary response, such as 50% of max, and the first intensity level that corresponds to a particular level of the first pupillary response, such as 50% of max.

In another embodiment, the one or more routines may be further adapted to turn the first light source on and off at a first predetermined interval while the intensity level is being increased, and turn the second light source on and off at a second predetermined interval while the intensity level is being increased. The first light source may be increased to a maximum level before the second light source is turned on and the intensity level thereof is increased. Also, the one or more routines may be further adapted to turn the first light source on and off at a predetermined interval at a set intensity level while the intensity level of the second light source is increased, wherein the first and second light sources are synchronized such that the first light source is turned on when the second light source is turned off and vice versa. Furthermore, the one or more routines may be adapted to stop increasing the intensity level of the second light source when it is determined that the pupil is no longer changing, wherein the second light source is at a maximum level and the severity level indication is based on the set intensity level and the maximum level of the second light source.

The light source may include a plurality of light emitting diodes. For example, the first light source may be one or more first light emitting diodes and the second light source may be a plurality of annularly arranged second light emitting diodes. Alternatively, the light source may include a computer screen. For example, the first light source may be a first portion of a computer screen and the second light source may be a second, annular portion of the computer screen.

The present invention also relates to a method of screening for retinal disease in an eye of a patient including steps of directing a first light at a first portion of the retina, directing a second light at a second portion of the retina, measuring a first pupillary response of the eye when the first light is directed at the first portion of said retina, measuring a second pupillary response of the eye when the second light is directed at the second portion of the retina, and generating an indication of a severity level of the retinal disease using the first pupillary response and the second pupillary response.

The first portion may be a central portion of the retina and the second portion may be a midperipheral portion of the retina. In addition, the second light may be an annulus light. In one particular embodiment, the first portion of the retina is about a central ten degrees of the retina, and the second portion of the retina is an annulus of the retina that is inclusive of about twenty to fifty degrees eccentric to a fovea of the eye.

Furthermore, the step of directing the first light may further include increasing an intensity level of the first light over a plurality of first intensity levels, the step of measuring the first pupillary response may further include making a first pupillary measurement at each of the first intensity levels, the step of directing the second light may further include increasing an intensity level of the second light over a plurality of second intensity levels, and the step of measuring the second pupillary response may further include making a second pupillary measurement at each of the second intensity levels. In this case, the first pupillary response may be based on the first pupillary measurements and the second pupillary response may be based on the second pupillary measurements.

The severity indication generating step may include generating a ratio based on one of the first intensity levels and one of the second intensity levels, such as a ratio of the second intensity level to the first intensity level. In addition, the intensity levels used may be one of the second intensity levels corresponding to a first particular level of the second pupillary response and one of the first intensity levels corresponding to a second particular level of the first pupillary response, with the first and second particular levels being equal to one another. Such levels may be fifty percent of a maximum pupillary response.

In one particular embodiment of the method, the step of directing the first light may further include turning the first light on and off at a first predetermined interval while the intensity level of the first light is increased, and the step of directing the second light may further include turning the second light on and off at a second predetermined interval while the intensity level of the second light is increased. Also, the step of increasing the intensity level of the first light may further include increasing the intensity level of the first light to a first maximum level before the second light is turned on and the intensity level of the second light is increased. The step of directing the first light may also further include turning the first light on and off at a third predetermined interval at a set intensity level while the intensity level of the second light is increased, wherein the first and second lights are synchronized such that the first light is on when the second light is off and vice versa. The method may include no longer increasing the intensity level of the second light when it is determined that a pupil of said eye is no longer changing, wherein the second light will have a maximum level and generating a ratio based on the set intensity level and the maximum level of the second light.

It is an object of this invention to provide a method and apparatus for screening for retinopathy that provide an objective and quantitative indication of the severity level of retinal disease.

It is a further object of this invention to provide a method and apparatus for screening for retinopathy that is noninvasive.

It is a further object of this invention to provide a method and apparatus for screening for retinopathy that requires minimal cooperation of the patient.

It is a further object of this invention to provide a method and apparatus for screening for retinopathy that requires limited technician skills.

It is a further object of this invention to provide a method and apparatus for screening for retinopathy that can yield an immediate clinical assessment.

BRIEF DESCRIPTION OF THE DRAWINGS

These and other advantages of the present invention will become readily apparent upon consideration of the following detailed description and attached drawings, wherein:

FIGS. 5A, 5B and 5C are isometric cross-sectional views of the eye showing different retinal portions;

FIG. 5D is a side cross-sectional view of the eye showing different retinal portions;

DETAILED DESCRIPTION OF THE PREFERRED EMBODIMENTS

In healthy people having normal vision, different portions or areas of the retina, such as the central portion and the midperipheral portion, are generally equally sensitive to light. As a result, light of a particular intensity that is independently incident upon each of those different regions will produce generally the same pupillary response, i.e., the pupil will constrict to the same degree. In contrast, as discussed elsewhere herein, certain eye diseases cause reduced sensitivity to light in particular retinal areas as compared to others. For example, in diabetic retinopathy, the sensitivity of both the central and midperipheral portions of the retina to light are reduced, with the sensitivity of the midperipheral portion being reduced to a much greater degree.

Figure 1:
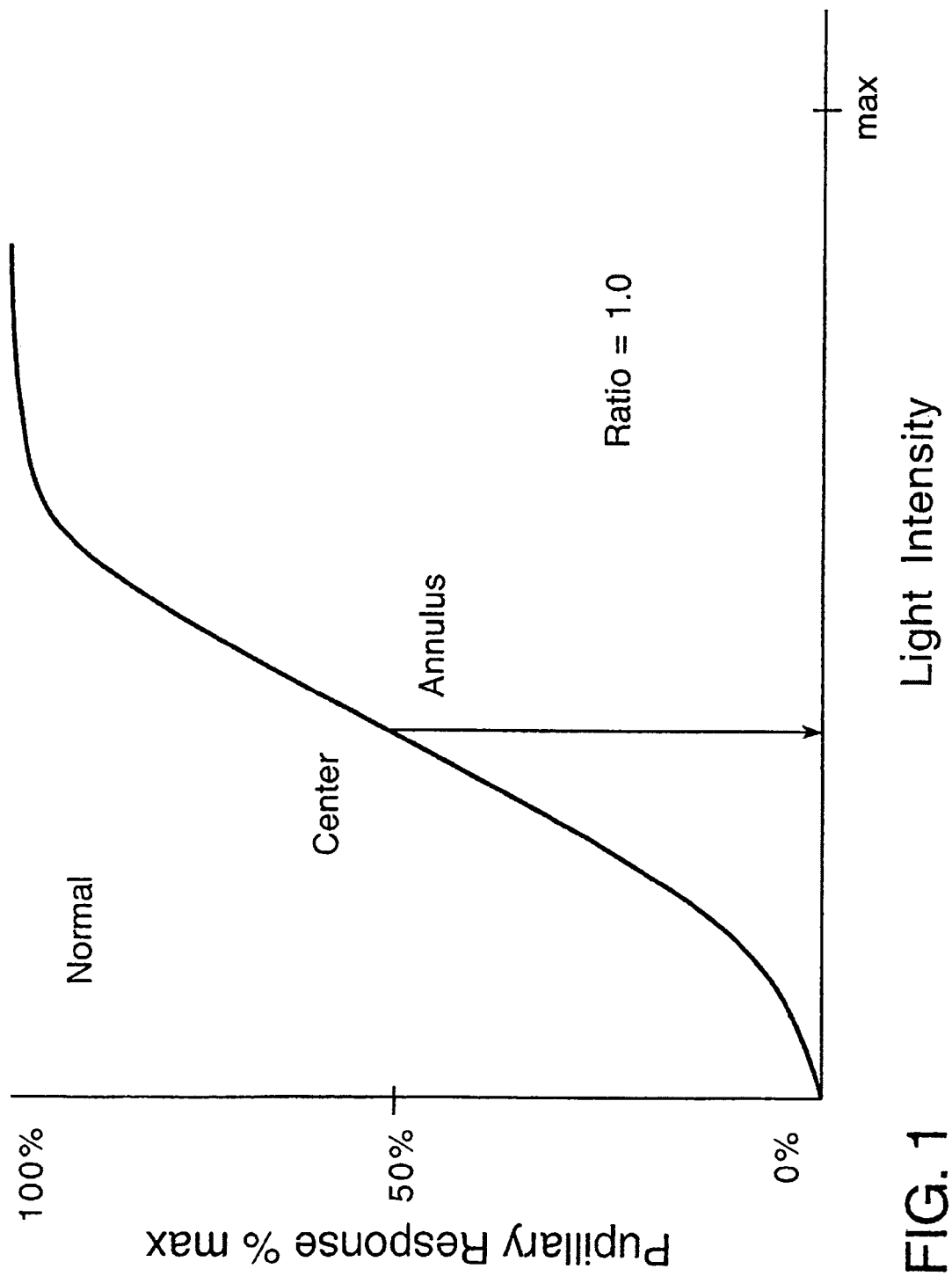
FIG. 1 is a graph of pupillary response versus center and annulus light intensity for a person having normal vision.
Figure 2:
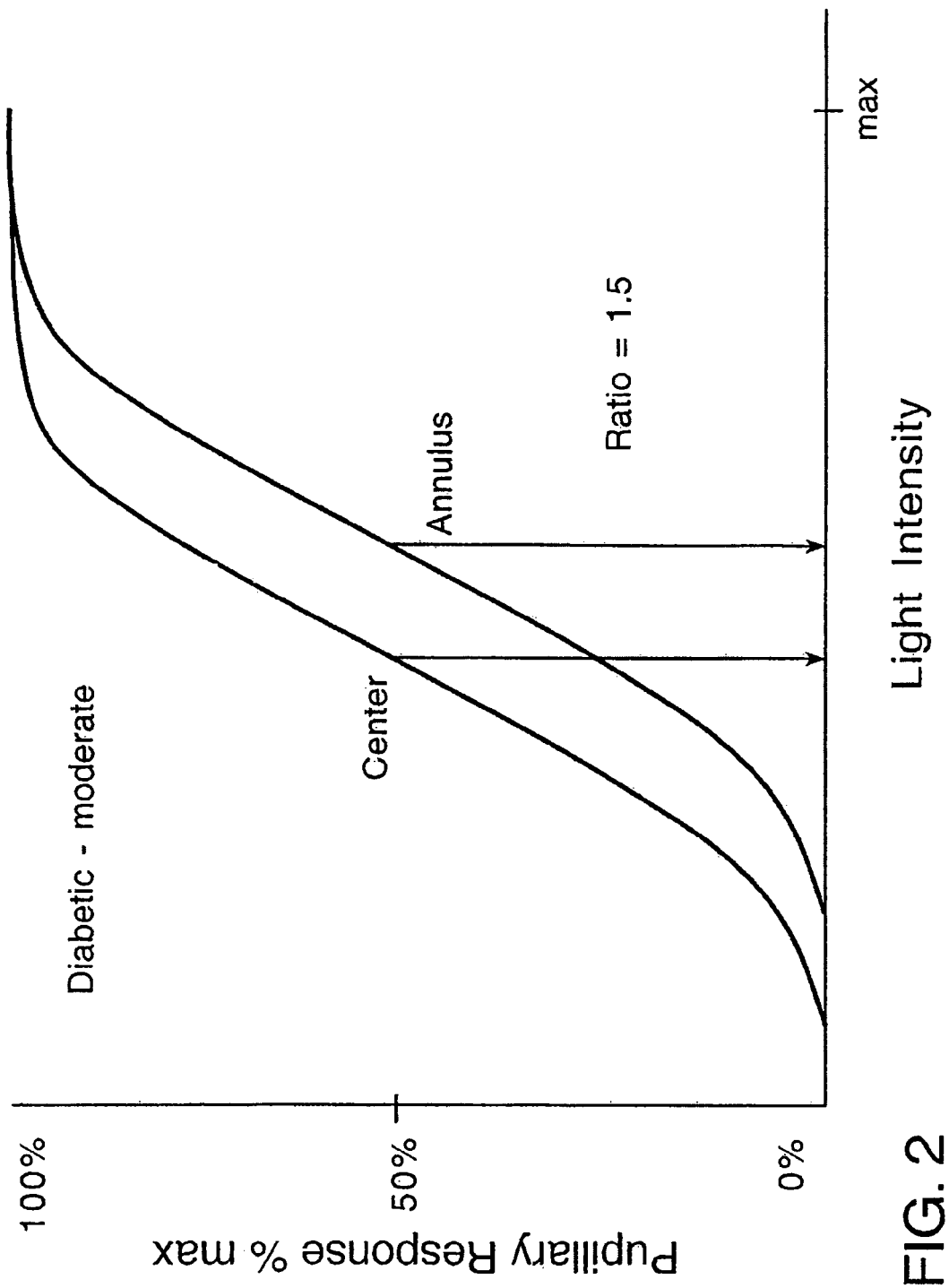
FIG. 2 is a graph of pupillary response versus center and annulus light intensity for a person having moderate retinal ischemia.
Figure 3:
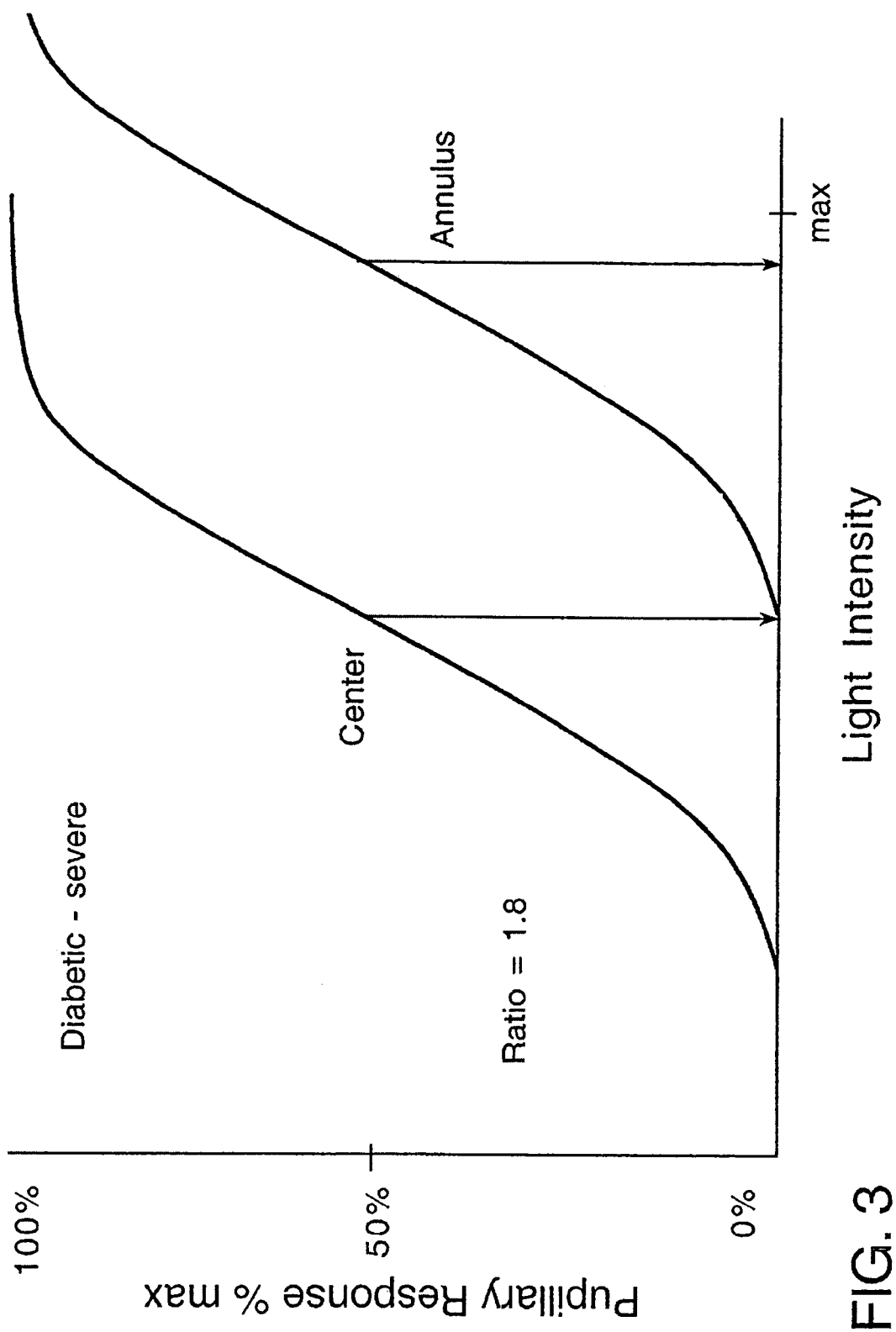
FIG. 3 is a graph of pupillary response versus center and annulus light intensity for a person having severe retinal ischemia.

As is known, the sensitivity of the retina to light may be observed by measuring the pupillary response to light. FIG. 1 is a graph of pupillary response, as a percentage of maximum pupil constriction, versus light intensity for both a center light focused on the central portion of the retina and an annulus light focused on the midperipheral portion of the retina for a person having normal vision. As seen in FIG. 1, the pupillary response caused by each light source is generally the same for all light intensities (the two curves lay on top of one another). Thus, as shown in FIG. 1, there is a 1 to 1 ratio of the intensity of the annulus light that causes a 50% pupillary response to the intensity of the center light that causes a 50% pupillary response. FIG. 2 is a similar graph for a person having a moderate diabetic condition with moderate retinal ischemia. As seen in FIG. 2, the curves for both the center light and the annulus light have moved to the right, meaning that the light sensitivity of both the central portion of the retina and the midperipheral portion of the retina has decreased (it takes a greater light intensity in each case to produce the same pupillary responses shown in FIG. 1). However, as also seen in FIG. 2, the curve for the annulus light has moved farther to the right, meaning that the light sensitivity of the midperipheral portion of the retina has been reduced to a greater degree than that of the central portion of the retina. Thus, there is no longer a 1 to 1 ratio of intensities causing a 50% pupillary response, as was the case in FIG. 1. Instead, the ratio is something greater than 1, such as the ratio of 1.5 shown in FIG. 2. FIG. 3 is yet another similar graph for a person having a severe diabetic condition with severe retinal ischemia wherein both the center light curve and, to an even larger degree, the annulus light curve have moved even farther to the right. The result is a larger ratio of intensities causing a 50% pupillary response, such as the ratio of 1.8 shown in FIG. 3.

The present invention utilizes pupillometry, and in particular the differing pupillary response characteristics demonstrated in FIGS. 1, 2 and 3, to obtain an objective, quantitative indication of the severity of diseases that affect different parts of the retina differently, such as diabetic retinopathy. More specifically, the present invention measures pupil responses to compare the relative sensitivities of different portions of the retina to light and correlates the relative sensitivities with the level of severity of a particular disease.

Figure 4:
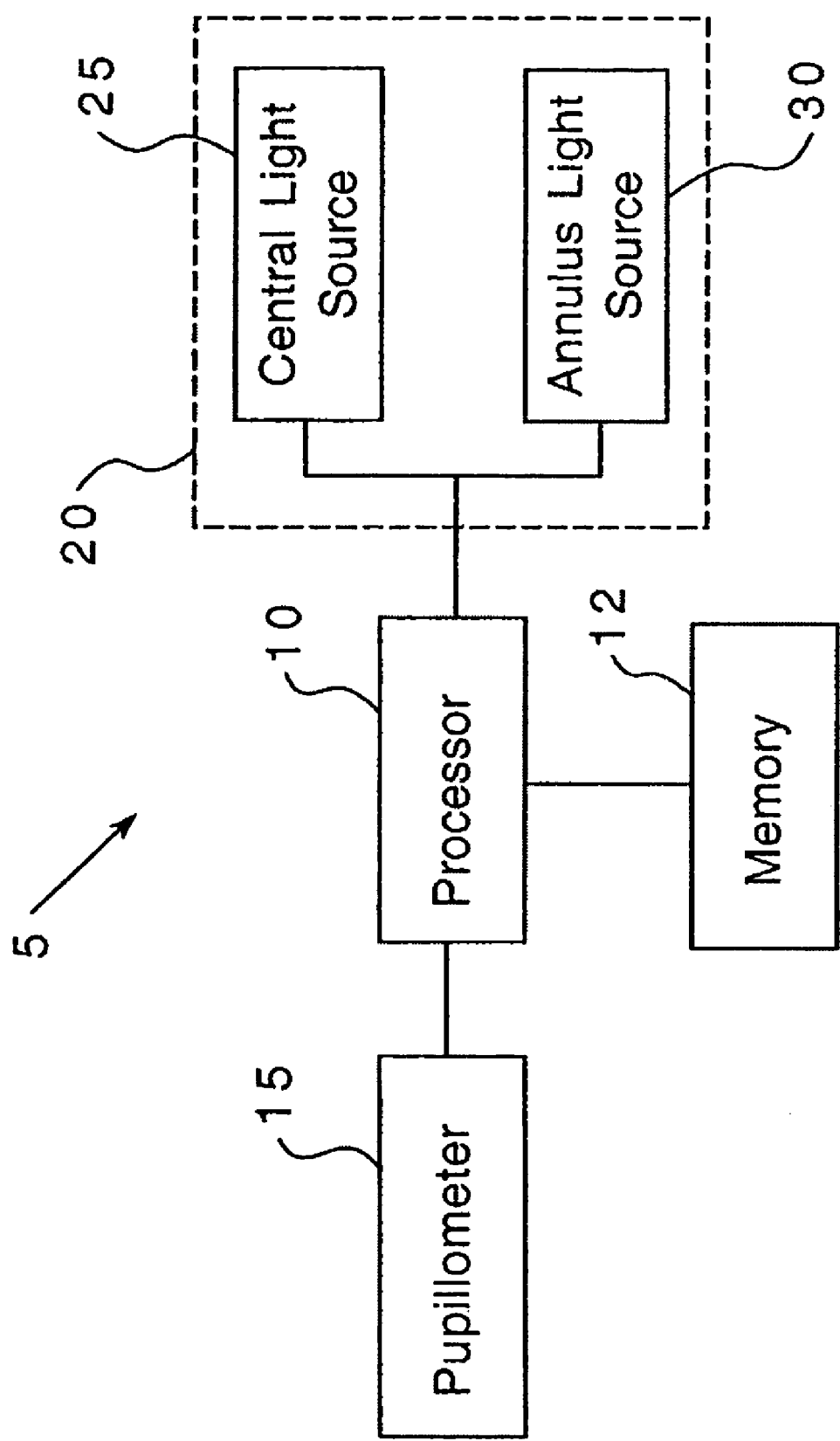
FIG. 4 is a block diagram of an apparatus for screening for retinopathy according to the present invention.

FIG. 4 is a block diagram of an apparatus 5 for screening for retinopathy according to the present invention that provides an objective, quantitative measurement of the severity of retinal disease and associated disease features, such as diabetic retinopathy and retinal ischemia. Apparatus 5 includes processor 10, which may be, without limitation, a microprocessor, and a memory 12 in communication therewith. Memory 12 can be any of a variety of types of internal and/or external storage media such as, without limitation, RAM, ROM, EPROM(s), EEPROM(s), and the like, that provide a storage register for data storage such as in the fashion of an internal storage area of a computer, and can be volatile memory or nonvolatile memory. Also, processor 10 and memory 12 may be separate electronic components or may be combined in a single electronic component. Memory 12 further includes a number of applications or routines executable by processor 10 for the processing of data as described herein. Such applications or routines can be in any variety of forms, such as, without limitation, software, firmware, and the like.

As seen in FIG. 4, pupillometer 15 is in electronic communication (wired or wireless) with processor 10. Pupillometer 15 is a device that is capable of automatically measuring the diameter of the pupil of the eye, even as that diameter changes when the pupil dilates and/or constricts. Many such devices are well known in the art, and typically employ an infrared light source that is directed at the pupil of the subject and an infrared detector, such as an infrared camera, positioned to receive infrared light that is reflected by the eye to make measurements of the diameter of the pupil. Such devices employ sophisticated, known software applications for converting the infrared light signals received by the infrared detector into pupil diameter measurements. Examples of such known devices include the Oasis™ Colvard pupillometer sold by Oasis Medical, Inc. of Glendora, Calif., the MCJ Eye Check™ FC2000 pupillometer sold by Barenco of Clare, County Kildare, Ireland, the NeurOptics™ pupillometer sold by Becton, Dickinson and Company of Franklin Lakes, N.J., and the P20002A pupillometer manufactured by Procyon Instruments Ltd., and distributed by Keeler Instruments of Broomall, Pa. Pupillometers such as those listed are most frequently used to measure the pupil sizes of patients in both light and dark conditions prior to refractive surgery.

Referring to FIG. 4, light source 20, which includes a plurality of light sources, is also in electronic communication with processor 10. In the particular embodiment described in connection with FIGS. 4, 6, and 7, which may be used to provide an indication of the severity of diabetic retinopathy and retinal ischemia, light source 20 includes central light source 25 and annulus light source 30. Each light source 25, 30 may comprise, among other known devices, a number of light emitting diodes arranged in a suitable manner or an appropriately sized image formed on a computer screen such as a liquid crystal display. Apparatus 5 is configured such that central light source 25 is directed at the central portion of the retina and annulus light source 30 is directed at the midperipheral portion of the retina when the patient focuses on a particular location. In the preferred embodiment, central light source 25 is adapted to illuminate a central portion consisting of about 10 degrees of the retina, and annulus light source 30 is adapted to illuminate a 360 degree midperipheral annulus portion of the retina that is inclusive of about 20 to 50 degrees eccentric to the fovea. For illustrative purposes, these preferred regions are demonstrated in FIGS. 5A, 5B and 5C, each of which are cross-sectional isometric views of eye 35. FIG. 5A is a view of eye 35 showing retina 40, FIG. 5B is a view of eye 35 showing retina 40 with central portion 45 highlighted, and FIG. 5C is a view of eye 35 showing retina 40 with midperipheral annulus portion 50 highlighted. In addition, FIG. 5D is a cross-sectional side view showing eye 35 including retina 40 having central portion 45 and midperipheral annulus portion 50.

Figure 6:
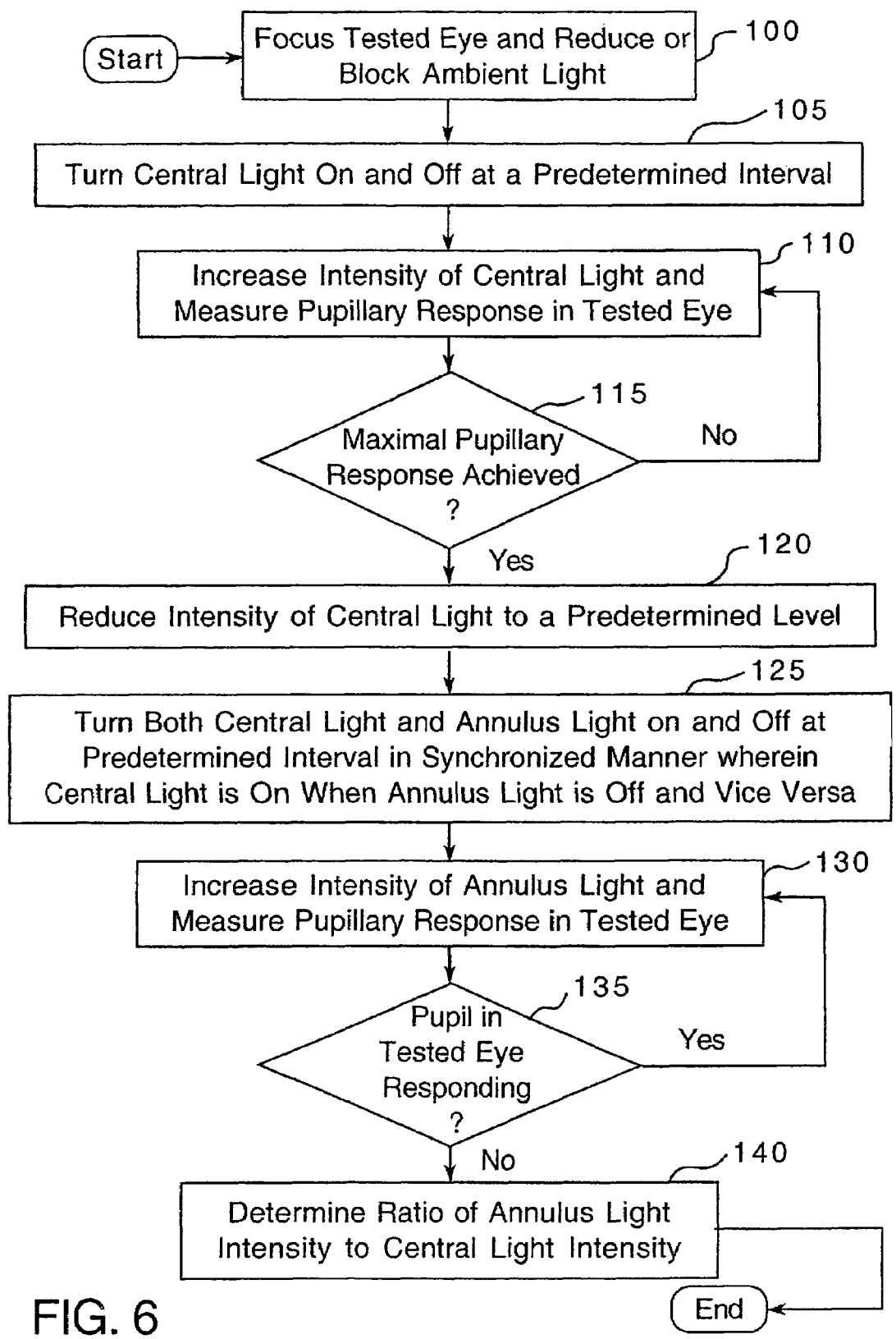
FIG. 6 is a flowchart illustrating a method of screening for retinopathy using the apparatus shown in FIG. 1 or FIG. 8 according to the present invention.

FIG. 6 is a flowchart depicting a method of screening for retinopathy according to one embodiment of the present invention that provides an objective, quantitative indication of the severity of retinal disease utilizing, for example, apparatus 5 shown in FIG. 4 (or, alternatively, apparatus 60 shown in FIG. 8 and described below). As will be appreciated, the method shown in FIG. 6 may be implemented in one or more routines embodied in software that is stored in memory 12 and executable by processor 10 of apparatus 5.

The method begins at step 100, where the patient's face is brought into proximity with apparatus 5 and the eye being tested (the "tested eye") is focused on a particular location such that central light source 25 is directed at and will illuminate the desired central portion of the retina, and such that annulus light source 30 is directed at and will illuminate the desired midperipheral portion of the retina. Ambient room light is either reduced or blocked from exposure to both eyes by a surrounding blocking structure or mask. Initially, both central light source 25 and annulus light source 30 are off. The eye not being tested is blocked from the testing light sources. In one embodiment, only the pupillary responses of the tested eye are measured, while in another embodiment, the pupillary responses of both eyes are measured simultaneously while the light sources are activated for one or the other eye.

Next, at step 105, central light source 25 is turned on and off at a regular, predetermined interval at an initial intensity level. Next, the intensity level of central light source 25 is increased a predetermined amount, and the pupillary response of the pupil of the tested eye is measured (in terms of the diameter of the pupil) by pupillometer 15. A determination is then made, at step 115, as to whether a maximal pupillary response has been achieved, meaning that the pupillary response is no longer changing (pupil is no longer becoming more constricted) when light intensity is increased. If the answer at step 115 is no, then the method returns to step 110 where the intensity level is increased and the pupillary response is again measured. Thus, as will be appreciated, steps 110 and 115 will result in pupillary response being measured at a multiplicity of light intensity levels as the light intensity is increased until a maximal pupillary response is achieved. The data that is obtained in these steps may be used to construct a graph of pupillary response versus light intensity for central light source 25 similar to those shown in FIGS. 1, 2 and 3.

If, however, the answer at step 115 is yes (a maximal pupillary response has been achieved), then, at step 120, the intensity of central light source 25 is reduced to a predetermined level, preferably to about 50% of the intensity level when the maximal pupillary response was achieved (step 115), although other levels, such as 75%, may also be used.

Next, at step 125, both central light source 25 and annulus light source 30 are turned on and off at a predetermined interval in a synchronized manner wherein central light source 25 is on when annulus light source 30 is off and vice versa. The intensity level of central light source 25 is maintained at the level set at step 120, and the intensity level of annulus light source 30 is set to an initial value. Then, at step 130, the intensity level of annulus light source 30 is increased by a predetermined amount, and the pupillary response in the tested eye due to light from annulus light source 30 is measured by pupillometer 10. At step 135, a determination is then made as to whether the pupil in the tested eye is still responding (i.e., diameter is changing) to the changing light from the two sources 25 and 30. If the answer at step 135 is yes, the method returns to step 130 where the light intensity of annulus light source 30 is increased and the pupillary response is again measured. As will be appreciated, steps 130 and 135 will result in the pupillary response due to annulus light source 30 being measured at a multiplicity of light intensity levels, and the data obtained may be used to construct a graph of pupillary response versus light intensity for annulus light source 30.

If the answer at step 135 is no (meaning the pupil in the tested eye is static and no longer responding), then, at step 140, the ratio of the current intensity level of the annulus light source 30 to the intensity level of the central light source set at step 130 is obtained. Alternatively, a similar ratio may be obtained from the data gathered at steps 110 and 115 and 130 and 135 based on the intensity levels of each light source at a chosen pupillary response level, such as the intensity level of each light source that caused 50% of the maximum response.

Such a ratio will be an indication of the reduced retinal sensitivity to light of the midperipheral portion of the retina as compared to the central portion of the retina, and thus an indication of the severity level of a retinal disease such as diabetic retinopathy. Through experimentation, a range of ratio values may be established for what is to be considered a normal healthy retina that is not in need of further testing or treatment. In addition, a threshold ratio value may be established such that, if a patient is determined to have a ratio above that value, the patient is considered to have a retinal problem and should undergo further testing and/or treatment for retinal disease. The patient's ratio may be tracked over time to monitor changes in the ratio indicating the progression of a particular retinal disease condition. Also, various ranges above a threshold ratio value can be established to indicate relative severity levels of retinal disease, such as mild, moderate, severe and/or advanced disease.

In addition, because a ratio of light intensities from different parts of the retina is used as the severity indicator in the present invention, it will be appreciated that eye conditions, such as cataracts, that adversely effect light transmission in the eye will not adversely effect the measurement. This is the case because the adverse eye condition will effect the light transmission at both parts of the retina equally such that the calculated ratio will not be effected (less light will reach each part of the retina and, as a result, pupillary response will be reduced equally at each part of the retina). The same can be said in the event that pupil response is affected for some reason, such as in a person that is taking a drug that decreases pupil response. The same decreased pupil response will be present when both retinal areas are stimulated, and thus the calculated ratio will not be adversely affected.

Figure 7:
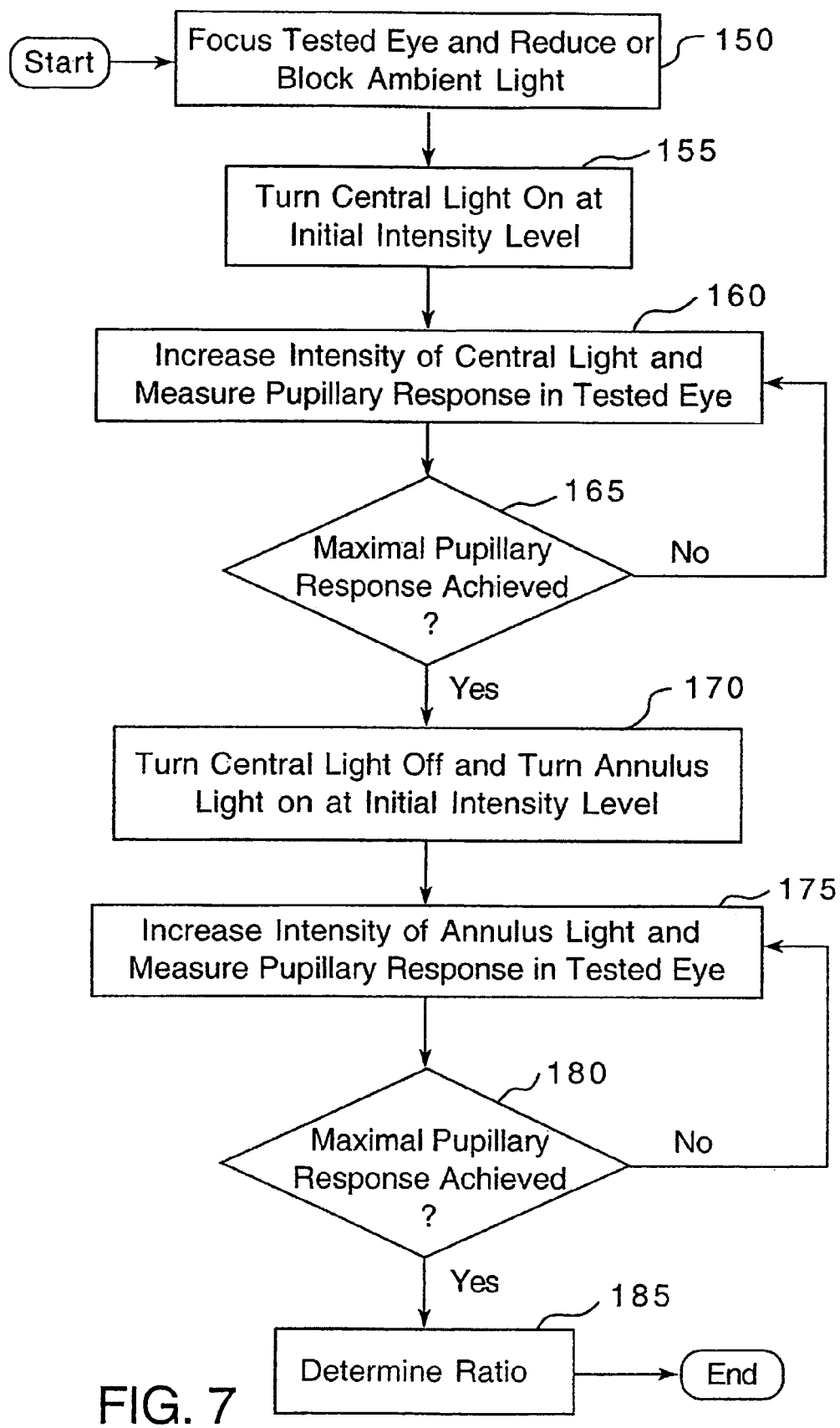
FIG. 7 is a flowchart illustrating a alternate method of screening for retinopathy using the apparatus shown in FIG. 1 or FIG. 8 according to the present invention.

FIG. 7 is a flow chart depicting a method of screening for retinopathy according to an alternate embodiment of the present invention that provides an objective, quantitative indication of the severity of retinal disease utilizing apparatus 5 shown in FIG. 4. As will be appreciated, the method shown in FIG. 7 may be implemented in one or more routines embodied in software that is stored in memory 12 and executable by processor 10 of apparatus 5.

This alternative method begins at step 150, where the patient's face is brought into proximity with apparatus 5 and the tested eye is focused on a particular location such that central light source 25 is directed at and will illuminate the desired central portion of the retina, and such that annulus light source 30 is directed at and will illuminate the desired midperipheral portion of the retina. Next, at step 155, central light source 25 is turned on at an initial intensity level (annulus light source 30 is off). Then, at step 160, the intensity of central light source 25 is increased a predetermined amount, and the pupillary response of the pupil of the tested eye is measured by pupillometer 15. A determination is then made, at step 165, as to whether a maximal pupillary response has been achieved. If the answer at step 165 is no, then the method returns to step 110 where the intensity level is increased and the pupillary response is again measured. Thus, as will be appreciated, steps 160 and 165 will result in pupillary response being measured at a multiplicity of light intensity levels as the light intensity is increased. The data that is obtained in these steps may be used to construct a graph of pupillary response versus light intensity for central light source 25 similar to those shown in FIGS. 1, 2 and 3.

If, however, the answer at step 165 is yes, then, at step 170, the central light source 25 is turned off and the annulus light source 30 is turned on at an initial intensity level. Next, at step 175, the intensity of annulus light source 30 is increased by a predetermined amount, and the pupillary response in the tested eye due to light from annulus light source 30 is measured by pupillometer 10. At step 180, a determination is then made as to whether a maximal pupillary response has been achieved. If the answer at step 180 is no, the method returns to step 175 where the light intensity of annulus light source 30 is increased and the pupillary response is again measured. As will be appreciated, steps 175 and 180 will result in the pupillary response due to annulus light source 30 being measured at a multiplicity of light intensity levels, and the data obtained may be used to construct a graph of pupillary response versus light intensity for annulus light source 30. If the answer at step 180 is yes, then, at step 140, a ratio may be obtained from the data gathered at steps 160 and 165 and 175 and 180 based on the intensity levels of each light source 25, 30 at a chosen pupillary response level, such as the intensity level of each light source 25, 30 that caused 50% of the maximum pupillary response.

As was the case with FIG. 6, this ratio will be an indication of the reduced retinal sensitivity to light of the midperipheral portion of the retina as compared to the central portion of the retina, and thus is an indication of the severity level of a retinal disease such as diabetic retinopathy. It will be appreciated that, while FIG. 7 showing pupillary response to central light source 25 being measured before pupillary response to central light source 30 is measured; the order of such measurements may be reversed without departing from the scope of the present invention. In addition, as a further alternative, central light source 25 may, at steps 155 and 160, be turned on and off at a predetermined interval while pupillary response is being measured. Similarly, annulus light source 30 may, at steps 170 and 175, be turned on and off at a predetermined interval while pupillary response is being measured.

Figure 8:
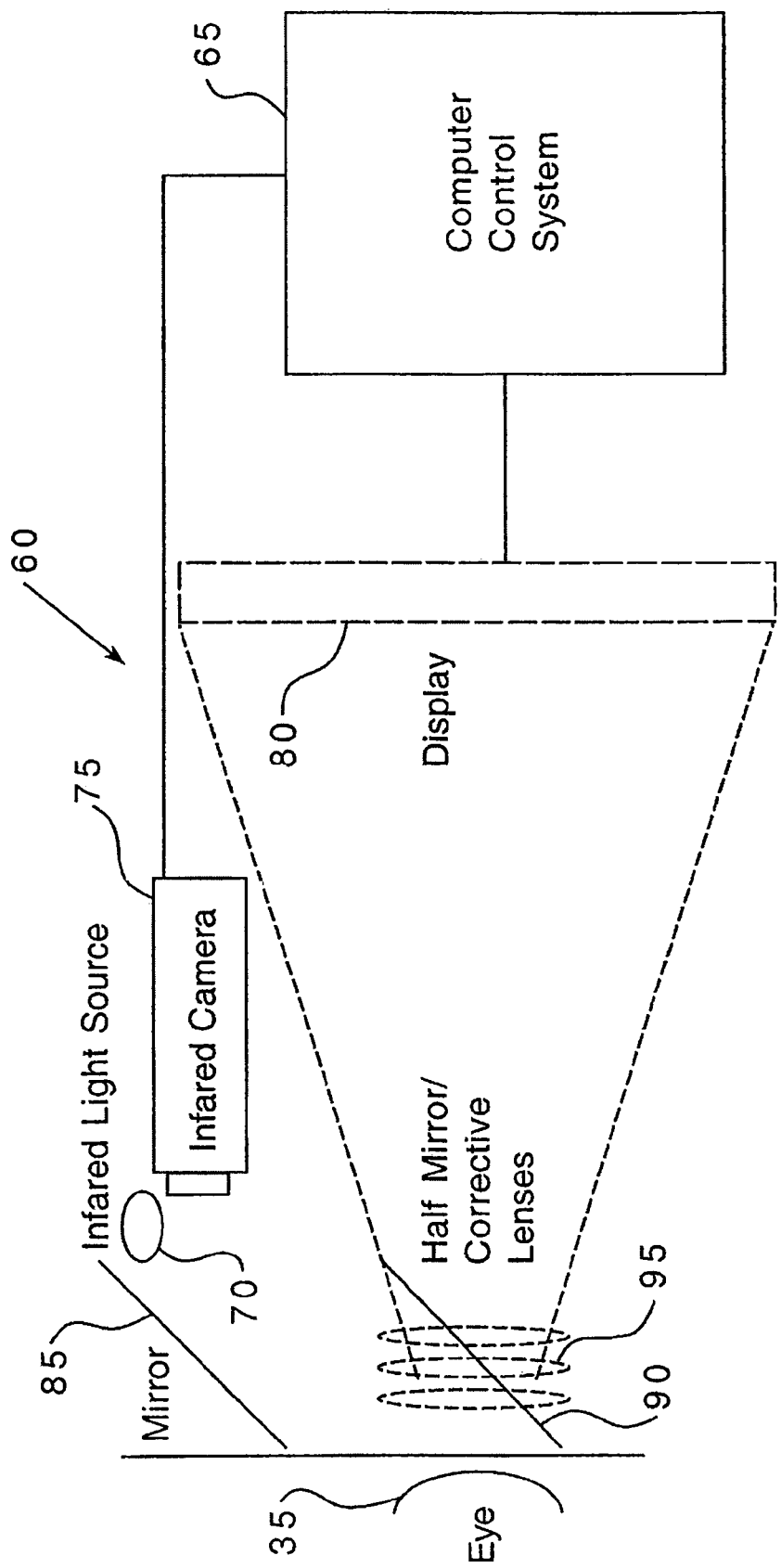
FIG. 8 is a block diagram of one particular embodiment of an apparatus for screening for retinopathy according to the present invention.

FIG. 8 is a block diagram of an apparatus 60 for screening for retinopathy according to one particular embodiment of the present invention that provides an objective, quantitative measurement of the severity of retinal disease and associated disease features, such as diabetic retinopathy and retinal ischemia. Apparatus 60 includes a computer control system 65 which includes a processor and a memory for storing executing one or more routines for implementing the present invention as described herein. In particular, computer control system 65 is adapted to store and execute one or more outlines for controlling the various components of apparatus 60 described below to measure pupillary response and provide an indication of retinal disease according to the present invention, such as is described in connection with FIGS. 6 and 7. Infrared light source 70 and infrared camera 75 are in electronic communication with computer control system 65. Infrared light source 70 and infrared camera 75, along with appropriate software stored in computer control system 65, are able to function as a pupillometer for measuring pupillary response of eye 35. Display 80 is also in electronic communication with computer control system 65. Display 80 is adapted to, under the control of computer control system 65, generate and display an image consisting of a central light source and an annulus light source. The image displayed on display 80 is configured such that the central light source portion thereof is directed at the central portion of the retina and the annulus light source portion thereof is directed at the midperipheral portion of the retina when the patient focuses on a particular location. In addition, apparatus 60 includes mirror 85, half mirror 90 and corrective lenses 95 which cooperate to focus the image from display 80 onto eye 35 and to enable infrared light source 70 and infrared camera 75 to transmit and receive infrared light to measure pupillary response from a location that is not in the way of the path of the image from display 80. As noted above, apparatus 60 may be used to implement the method of the present invention, embodiments of which are shown in FIGS. 6 and 7. In an alternative embodiment, the monitoring infrared camera may positioned behind the fixation point used for the two light sources, whatever they may be.

Moreover, in the embodiments described above, it is contemplated that a single pupillometer and a single light source are used to make measurements on each eye independently, one after the other, with the patient moving or adjusting his or her position to allow the measurements to be made. It should be appreciated, however, that it is possible to provide an apparatus having two pupillometers and/or two light sources such that one pupillometer and one light source may be oriented toward one eye while the other pupillometer and light source are simultaneously oriented toward the other eye. With such a configuration, measurements can be made on each eye independently without requiring the patient to move or change position. In addition, it is known that, in a healthy person with healthy optic nerves, light stimulation in only a single eye should produce the identical pupillary response in both eyes even though the other eye is not being similarly stimulated. If this does not happen in a patient, it is typically a sign that the patient has optic nerve damage in one eye. Thus, an apparatus having two pupillometers, one focused on each eye, as described above may be used as a device for screening for optic nerve problems. In particular, as the tested eye is being stimulated as described herein to determine an indication of the severity of retinopathy in that eye, the pupillary response in the other, non-tested eye can be simultaneously measured. If the optic nerve in the non-tested eye is healthy, the same pupillary response should be observed in the non-tested eye as is observed in the tested eye, and any difference in observed pupillary response will be an indication of optic nerve damage in the non-tested eye. The same effect can be achieved with a single pupillometer that is rapidly measuring the pupil responses by both eyes in a rapidly alternating manner.

Thus, the present invention provides a method and an apparatus for screening for retinal disease and associated features, such as those that cause reduced light sensitivity in portions of the retina as is the case with retinal ischemia, that provide an objective and quantitative indication of the severity level of retinal disease. Unlike the prior art, the method and apparatus of the present invention is noninvasive, requires minimal cooperation of the patient, requires limited technician skills, and can yield an immediate clinical assessment (assessment will typically take approximately one minute or less per eye). The present invention may also be used for screening for optic nerve related problems.

While specific embodiments of the invention have been described in detail, it will be appreciated by those skilled in the art that various modifications and alternatives to those details could be developed in light of the overall teachings of the disclosure. For example, while a primary application of the present invention is to screen for diabetic retinopathy, the present invention may be used to screen for any retinal disease condition that affects different parts of the retina, and in particular light sensitivity in different parts of the retina, differently, such as sickle cell disease, retinitis pigmentosa, Eales disease, and radiation retinopathy, among others. In addition, the most effective or appropriate values for the various light intensity levels, light pulsing intervals and rates of intensity level increase and the like described herein are not presently known. Such values may be readily determined for the particular application in question based on experimentation. Accordingly, the particular arrangements disclosed are meant to be illustrative only and not limiting as to the scope of the invention which is to be given the full breadth of the claims appended and any and all equivalents thereof.

What is claimed is:

1. An apparatus for screening for retinal disease in an eye of a patient, said eye having a retina, comprising:
   a light source for directing a first light at a first portion of said retina and a second light at a second portion of said retina;
   a pupil measuring device for measuring a first pupillary response of said eye when said first light is directed at said first portion of said retina and a second pupillary response of said eye when said second light is directed at said second portion of said retina;
   a processor in electronic communication with said pupil measuring device; and
   a memory in electronic communication with said processor, said memory storing one or more routines executable by said processor, said one or more routines being adapted to generate an indication of a severity level of said retinal disease using said first pupillary response and said second pupillary response.

2. An apparatus according to claim 1, including said light source comprising a first light source for generating said first light and a second light source for generating said second light.

3. An apparatus according to claim 1, including said first portion being a central portion of said retina and said second portion being a midperipheral portion of said retina.

4. An apparatus according to claim 3, including said light source comprising a first light source for generating said first light and a second light source for generating said second light.

5. An apparatus according to claim 4, including said second light source being an annulus light source and said second light being an annulus light.

6. An apparatus according to claim 5, including said first light source comprising one or more first light emitting diodes and said second light source comprising a plurality of annularly arranged second light emitting diodes.

7. An apparatus according to claim 5, including said first light source comprising a first portion of a computer screen and said second light source comprising a second, annular portion of said computer screen.

8. An apparatus according to claim 3, including said first portion of said retina being about a central ten degrees of said retina, and said second portion of said retina being an annulus of said retina that is inclusive of about twenty to fifty degrees eccentric to a fovea of said eye.

9. An apparatus according to claim 1 including said pupil measuring device comprising an infrared light source and an infrared detector.

10. An apparatus according to claim 1, including said one or more routines being further adapted to:
    turn said first light source on and increase an intensity level of said first light over a plurality of first intensity levels, said pupil measuring device making a first pupillary measurement at each of said first intensity levels, said first pupillary response being based on said first pupillary measurements; and turn said second light source on and increase an intensity level of said second light over a plurality of second intensity levels, said pupil measuring device making a second pupillary measurement at each of said second intensity levels, said second pupillary response being based on said second pupillary measurements.

11. An apparatus according to claim 10, including said indication being a ratio that is generated based on one of said first intensity levels and one of said second intensity levels.

12. An apparatus according to claim 11, including said ratio being a ratio of said one of said second intensity levels to said one of said first intensity levels.

13. An apparatus according to claim 12, including said one of said second intensity levels corresponding to a first particular level of said second pupillary response and said one of said first intensity levels corresponding to a second particular level of said first pupillary response, said first and second particular levels being equal to one another.

14. An apparatus according to claim 13, including said first and second particular levels each being fifty percent of a maximum pupillary response.

15. An apparatus according to claim 10, including said one or more routines being further adapted to:
turn said first light source on and off at a first predetermined interval while said intensity level of said first light source is being increased; and
turn said second light source on and off at a second predetermined interval while said intensity level of said second light source is being increased.

16. An apparatus according to claim 15, including said one or more routines being further adapted to increase said first light source to a first maximum level before said second light source is turned on and said intensity level of said second light source is increased.

17. An apparatus according to claim 16, including said one or more routines being further adapted to turn said first light source on and off at a third predetermined interval at a set intensity level while said intensity level of said second light source is increased, wherein said first and second light sources are synchronized such that said first light source is turned on when said second light source is turned off and vice versa while said intensity level of said second light source is increased.

18. An apparatus according to claim 17, including said third predetermined interval being equal to said first predetermined interval.

19. An apparatus according to claim 17, including said one or more routines being adapted to stop increasing said intensity level of said second light source when it is determined that a pupil of said eye is no longer changing.

20. An apparatus according to claim 19, said second light source having a second maximum level when said intensity level is no longer being increased, said indication being based on said set intensity level and said second maximum level.

21. An apparatus according to claim 20, including said indication being a ratio of said second maximum level to said set intensity level.

22. An apparatus according to claim 16, including said one or more routines being adapted to stop increasing said intensity level of said second light source when it is determined that a pupil of said eye is no longer changing.

23. An apparatus according to claim 22, said second light source having a second maximum level when said intensity level is no longer being increased, said indication being based on said first maximum level and said second maximum level.

24. An apparatus according to claim 23, including said indication being a ratio of said second maximum level to said first maximum level.

25. An apparatus according to claim 1, including said first pupillary response and said second pupillary response each being based on a diameter of a pupil of said eye measured by said pupil measuring device.

26. An apparatus according to claim 1, including said light source comprising a plurality of light emitting diodes.

27. An apparatus according to claim 1, including said light source comprising a computer screen.

28. An apparatus according to claim 1, including said patient having a second eye having an optic nerve, said apparatus further comprising a second pupil measuring device for measuring a third pupillary response of said second eye when said first light is directed at said first portion of said retina of said eye and a fourth pupillary response of said second eye when said second light is directed at said second portion of said retina of said eye, said one or more routines being further adapted to perform one or both of a comparison of said first pupillary response to said third pupillary response and a comparison of said second pupillary response to said fourth pupillary response to determine whether said optic nerve is damaged.

29. A method of screening for retinal disease in an eye of a patient, said eye having a retina, comprising:
directing a first light at a first portion of said retina;
directing a second light at a second portion of said retina;
measuring a first pupillary response of said eye when said first light is directed at said first portion of said retina;
measuring a second pupillary response of said eye when said second light is directed at said second portion of said retina; and
generating an indication of a severity level of said retinal disease using said first pupillary response and said second pupillary response.

30. A method according to claim 29, including said first portion being a central portion of said retina and said second portion being a midperipheral portion of said retina.

31. A method according to claim 30, including said second light being an annulus light.

32. A method according to claim 30, including said first portion of said retina being about a central ten degrees of said retina, and said second portion of said retina being an annulus of said retina that is inclusive of about twenty to fifty degrees eccentric to a fovea of said eye.

33. A method according to claim 29, including:
said step of directing said first light further comprising increasing an intensity level of said first light over a plurality of first intensity levels;
said step of measuring said first pupillary response further comprising making a first pupillary measurement at each of said first intensity levels, said first pupillary response being based on said first pupillary measurements;
said step of directing said second light further comprising increasing an intensity level of said second light over a plurality of second intensity levels; and
said step of measuring said second pupillary response further comprising making a second pupillary measurement at each of said second intensity levels, said second pupillary response being based on said second pupillary measurements.

34. A method according to claim 33, including said generating step comprising generating a ratio based on one of said first intensity levels and one of said second intensity levels, said indication being said ratio.

35. A method according to claim 34, including said ratio being a ratio of said one of said second intensity levels to said one of said first intensity levels.

36. A method according to claim 35, including said one of said second intensity levels corresponding to a first particular level of said second pupillary response and said one of said first intensity levels corresponding to a second particular level of said first pupillary response, said first and second particular levels being equal to one another.

37. A method according to claim 36, including said first and second particular levels each being fifty percent of a maximum pupillary response.

38. A method according to claim 33, including said step of directing said first light further comprising turning said first light on and off at a first predetermined interval while said intensity level of said first light is increased, and said step of directing said second light further comprising turning said second light on and off at a second predetermined interval while said intensity level of said second light is increased.

39. A method according to claim 38, including said step of increasing said intensity level of said first light further comprising increasing said intensity level of said first light to a first maximum level before said second light is turned on and said intensity level of said second light is increased.

40. A method according to claim 39, including said step of directing said first light further comprising turning said first light on and off at a third predetermined interval at a set intensity level while said intensity level of said second light is increased, wherein said first and second lights are synchronized such that said first light is on when said second light is off and vice versa while said intensity level of said second light is increased.

41. A method according to claim 39, including said step of directing said second light further comprising no longer increasing said intensity level of said second light when it is determined that a pupil of said eye is no longer changing.

42. A method according to claim 41, including said second light having a second maximum level when said intensity level is no longer being increased, and said generating step comprising generating a ratio based on said first maximum level and said second maximum level, said indication being said ratio.

43. A method according to claim 42, including said ratio being a ratio of said second maximum level to said first maximum level.

44. A method according to claim 40, including said step of directing said second light further comprising no longer increasing said intensity level of said second light when it is determined that a pupil of said eye is no longer changing.

45. A method according to claim 44, including said second light having a second maximum level when said intensity level is no longer being increased, and said generating step comprising generating a ratio based on said set intensity level and said second maximum level, said indication being said ratio.

46. A method according to claim 45, including said ratio being a ratio of said second maximum level to said set intensity level.

47. A method according to claim 29, including said step of measuring said first pupillary response and said step of measuring said second pupillary response each comprising measuring a diameter of a pupil of said eye.

48. A method according to claim 29, including said patient having a second eye having an optic nerve, said method further comprising measuring a third pupillary response of said second eye when said first light is directed at said first portion of said retina of said eye and a fourth pupillary response of said second eye when said second light is directed at said second portion of said retina of said eye, and performing one or both of a comparison of said first pupillary response to said third pupillary response and a comparison of said second pupillary response to said fourth pupillary response to determine whether said optic nerve is damaged.

* * * * *